United States Patent [19]
Asaka et al.

[11] Patent Number: 5,523,399
[45] Date of Patent: Jun. 4, 1996

[54] 5-O-DESOSAMINYLERYTHRONOLIDE DERIVATIVES

[75] Inventors: Toshifumi Asaka; Yoko Misawa; Masato Kashimura; Shigeo Morimoto; Katsuo Hatayama, all of Tokyo, Japan

[73] Assignee: Taisho Pharmaceutical Co., Ltd., Japan

[21] Appl. No.: 244,981
[22] PCT Filed: Dec. 15, 1992
[86] PCT No.: PCT/JP92/01713
   § 371 Date: Jun. 20, 1994
   § 102(e) Date: Jun. 20, 1994
[87] PCT Pub. No.: WO93/13115
   PCT Pub. Date: Jul. 8, 1993

[30] Foreign Application Priority Data

Dec. 27, 1991 [JP] Japan ................................... 3-346826
Jul. 27, 1992 [JP] Japan ................................... 4-199368
Oct. 19, 1992 [JP] Japan ................................... 4-279867

[51] Int. Cl.$^6$ ................................................. C07H 17/08
[52] U.S. Cl. ........................ 536/7.3; 536/7.2; 536/7.4
[58] Field of Search ........................ 536/7.1, 7.2, 7.3, 536/7.4

[56] References Cited

U.S. PATENT DOCUMENTS 3,923,784 12/1975 Kierstead et al. ........................ 260/210

FOREIGN PATENT DOCUMENTS 0216169 1/1987 European Pat. Off. .
4290893 10/1992 Japan .

Primary Examiner—Douglas W. Robinson
Assistant Examiner—Elli Peselev
Attorney, Agent, or Firm—Lorusso & Loud

[57] ABSTRACT

Provision of novel macrolide antibiotics having a strong antibacterial activity.
Construction:

Compounds represented by the formula:

which are obtained by introducing a carbamoyl group into 5-O-desosaminyl-6-O-methylerythronolide derivatives at the 3-position; and pharmaceutically acceptable acid addition salts thereof.

2 Claims, No Drawings

5-O-DESOSAMINYLERYTHRONOLIDE DERIVATIVES

TECHNICAL FIELD

The present invention relates to novel derivatives of an antibiotic erythromycin. More particularly, it relates to novel derivatives of 5-O-desosaminylerythronolide derivatives and pharmaceutically acceptable acid addition salts thereof.

BACKGROUND ART

Erythromycin is an antibiotic clinically widely used as an agent for curing infectious diseases caused by Gram-positive bacteria, some Gram-negative bacteria, mycoplasmas, etc. Many derivatives of erythromycin have been produced for improving the biological and/or pharmacodynamic characteristics of erythromycin. As 5-O-desosaminylerythronolide derivatives, 3-O-acyl-5-O-desosaminylerythronolide derivatives, for example, have been disclosed in U.S. Pat. No. 3,923,784. 5-O-desosaminylerythronolide derivatives, however, have been generally considered to be poor in antibacterial activity, and the antibacterial activity of the above-exemplified derivatives is also very weak. An object of the present invention is to provide novel antibiotics having a strong antibacterial activity.

DISCLOSURE OF THE INVENTION

The present inventors conducted various researches on the antibacterial activity of 5-O-desosaminylerythronolide derivatives and consequently found that compounds obtained by introducing a carbamoyl group into 5-O-desosaminylerythronolide derivatives at the 3-position have an unexpectedly strong antibacterial activity, whereby the present invention has been accomplished.

The present invention is 5-O-desosaminylerythronolide derivatives represented by the formula:

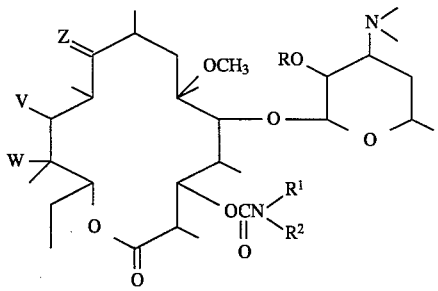

[wherein each of $R^1$ and $R^2$ is a hydrogen atom; a phenyl group; a substituted phenyl group having 1 to 5 substituents selected from halogen atoms, nitro groups and amino groups; a $C_1$–$C_{15}$ alkyl group; a $C_2$–$C_{15}$ alkyl group containing at least one nitrogen atom, oxygen atom or sulfur atom; a $C_7$–$C_{15}$ aralkyl group; or a $C_7$–$C_{15}$ aralkyl group containing at least one nitrogen atom, oxygen atom or sulfur atom; $R^1$ and $R^2$ being able to be groups which form a ring together with the adjacent nitrogen atom, Z is an oxygen atom or a group represented by the formula =N—O—$R^3$ (wherein $R^3$ is a hydrogen atom; a $C_1$–$C_8$ alkyl group; a $C_2$–$C_{18}$ alkyl group containing at least one nitrogen atom, oxygen atom or sulfur atom; a benzyl group; or a substituted benzyl group having 1 to 5 substituents selected from halogen atoms and $C_1$–$C_4$ alkyl groups), V is a hydroxyl group and W is a hydrogen atom or a hydroxyl group, or V and W represent together with the carbon atoms at the 11- and 12-positions a group represented by the formula:

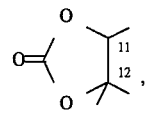

or a group represented by the formula:

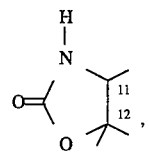

R is a hydrogen atom, a $C_2$–$C_{15}$ alkoxycarbonyl group, a $C_2$–$C_{15}$ alkoxycarbonyl group containing at least one oxygen atom in its alkyl moiety, a $C_2$–$C_{15}$ acyl group, a $C_2$–$C_{15}$ acyl group containing at least one oxygen atom, or a pyridylcarbonyl group] and pharmaceutically acceptable acid addition salts thereof.

In the present invention, the halogen atoms are fluorine, chlorine, bromine and iodine atoms. The term "alkyl group" means a linear one or a branched one. As the $C_2$–$C_{15}$ alkyl group containing at least one nitrogen atom, oxygen atom or sulfur atom, there can be exemplified aminoethyl group, dimethylaminoethyl group, benzylaminoethyl group, N-benzyl-N-methylaminoethyl group, dibenzylaminoethyl group, 2,3-dihydroxypropyl group, 3-aminopropyl group and 2-hydroxy-3-aminopropyl group. As the $C_7$–$C_{15}$ aralkyl group, there can be exemplified benzyl group, phenethyl group and diphenylmethyl group. As the $C_7$–$C_{15}$ aralkyl group containing at least one nitrogen atom, oxygen atom or sulfur atom, there can be exemplified nitrobenzyl group, methoxybenzyl group, methylthiobenzyl group, aminobenzyl group and dimethylaminobenzyl group. The term "$C_2$–$C_{15}$ alkoxycarbonyl group" means a substituted carbonyl group having an alkoxy group as the substituent, and there can be exemplified methoxycarbonyl group and benzyloxycarbonyl group. An oxygen atom in the alkyl moiety, xycarobonyl group can be exemplified. As the $C_2$–$C_{15}$ alkoxycarbonyl group containing at least one oxygen atom in its alkyl moiety, there can be exemplified methoxycarbonyl group, 2-methoxyethoxycarbonyl group, 2-[2-(2-methoxyethoxy)ethoxy]ethoxycarbonyl group, benzyloxycarbonyl group and 2-[2-(2-ethoxyethoxy)ethoxy]ethoxycarbonyl group. As the $C_2$–$C_{15}$ acyl group, there can be exemplified acetyl group, propionyl group and benzoyl group. The term "$C_2$–$C_{15}$ acyl group containing at least one oxygen atom" means a substituted acyl group having, for example, an alkoxycarbonyl group as the substituent, and ethylsuccinyl group can be exemplified. As the pharmaceutically acceptable acid addition salts, there can be exemplified acetates, propionates, butyrates, formates, trifluoroacetates, maleates, tartarates, citrates, stearates, succinates, ethylsuccinates, lactobionates, gluconates, glucoheptonates, benzoates, methanesulfonates, ethanesulfonates, 2-hydroxyethanesulfonates, benzenesulfonates, p-toluenesulfonates, laurylsulfates, malates, aspartates, glutaminates, adipates, cysteine salts, hydrochlorides, hydrobromides, phosphates, sulfates, hydroiodides, nicotinates, oxalates, picrates, thiocyanates, undecanoates, polyacrylates and carboxyvinyl polymer salts.

The compounds of the present invention include both those in which the coordination at the 3-position is natural (3S forms) and those in which the coordination at the 3-position is not natural (3R forms).

The compounds of the present invention can be produced, for example, as follows.

[Production process 1]

Process using 5-O-desosaminyl-6-O-methylerythronolide A as a starting material

Step (1);

5-O-desosaminyl-6-O-methylerythronolide A is reacted with an acid anhydride of the formula $R_2O$ (wherein R is as defined above except for hydrogen atom) or a halide of the formula R-X (wherein R is as defined above except for hydrogen atom, and X is an optional halogen atom) and a base in an inert solvent at 0° C. to 30° C., whereby there can be obtained a compound of the formula (a):

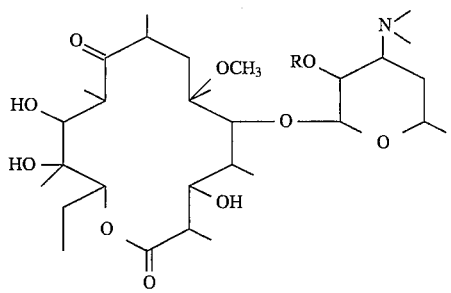

wherein R is as defined above. Here, as the suitable inert solvent, there are used dichloromethane, dichloroethane, acetone, pyridine, ethyl acetate, tetrahydrofuran, etc. As the acid anhydride or the halide, there are used anhydrides and halides of acetic acid, propionic acid, benzoic acid and pyridinecarboxylic acid, and carbonic acid ester halides such as 2-[2-(2-methoxyethoxy)ethoxy] ethyl chloroformate. As the base, there are used sodium hydrogencarbonate, sodium carbonate, potassium carbonate, triethylamine, pyridine, tributylamine, etc.

Step (2);

The compound obtained in step (1) is reacted with 1,1'-carbonyldiimidazole in an inert solvent at 0° C. to 80° C., after which an amine of the formula (wherein $R^1$ and $R^2$ are as defined above) is added and the reaction is carried out at 0° C. to 30° C., whereby there can be obtained a compound of the present invention of the formula (b):

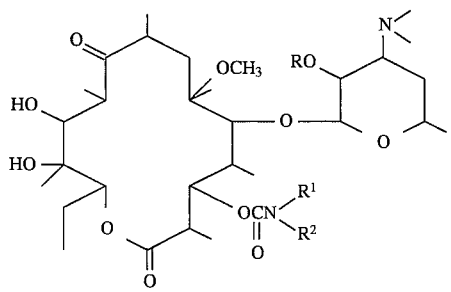

wherein R is as defined above. The compound of the formula (b) can be obtained also by using a suitable isocyanate and a base.

Step (3);

The compound obtained in step (2) is reacted in a lower alcohol at room temperature to 100° C., whereby there can be obtained a compound of the present invention of the formula (c):

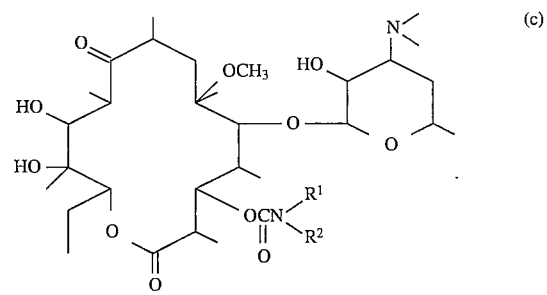

Here, as the lower alcohol, there are used methanol, ethanol, propanol, butanol, etc.

Step (4);

The compound obtained in step (2) is reacted with a reagent such as phosgene dimer or phosgene trimer under ice-cooling in a suitable inert solvent by the use of a base such as pyridine, whereby there can be obtained a compound of the formula (d):

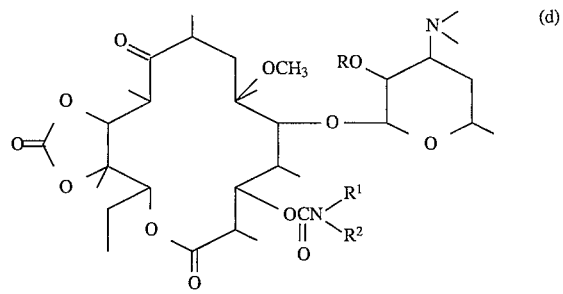

wherein, R is as defined above. Here, the suitable inert solvent is the same as used in step (1).

Step (5);

The compound of the formula (d) can be produced also by reacting the compound obtained in step (1), in the same manner as in step (4), adding an amine of the formula:

(wherein $R^1$ and $R^2$ are as defined above) in the same reactor, and then carrying out the reaction at 0° C. to room temperature. Then, the compound (d) is reacted in the same manner as in step (3), whereby there can be produced a compound of the present invention of the formula (e):

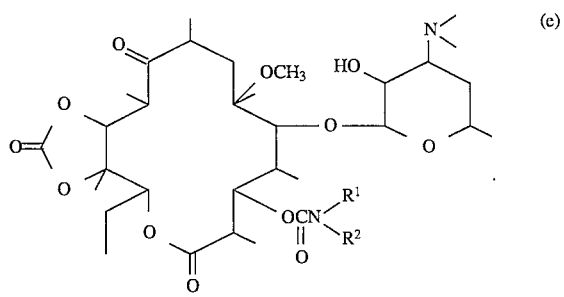

[Production process 2]

Process using 6-O-methylerythromycin A 9-oxime as a starting material

Step (6.);

6-O-methylerythromycin A 9-oxime is reacted with an acid in a lower alcohol at 0° C. to 30° C. to obtain a compound of the formula (f):

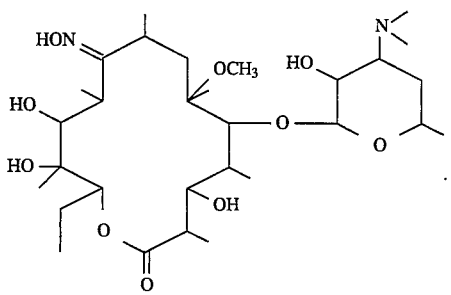

Here, the lower alcohol is the same as used in step (3). As the acid, there are used hydrochloric acid, hydrobromic acid, sulfuric acid, etc.

Step (7);

The compound obtained in step (6) is reacted with a reagent of the formula $R^3D$ (wherein $R^3$ is as defined above, and D is an optional halogen atom) and a base in an inert solvent at 0° C. to 30° C. to obtain a compound of the formula (g):

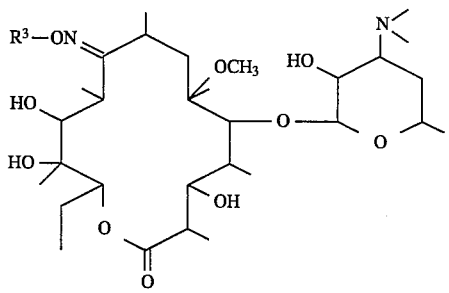

wherein $R^3$ is as defined above. Subsequently, this compound is reacted in the same manner as in steps (1), (2) and (3), whereby there can be produced a compound of the present invention of the formula (h):

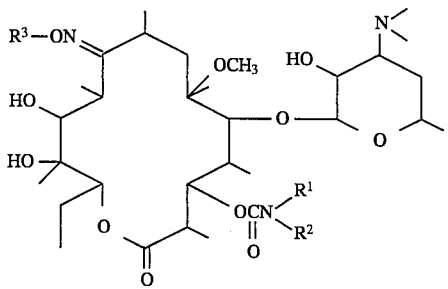

wherein $R^3$ is as defined above. Here, as the inert solvent, there are used dimethylformamide, N-methylpyrrolidone, tetrahydrofuran, acetonitrile and mixed solvents thereof. As the base, there are used sodium hydride, potassium hydroxide, sodium bistrimethylsilylamide, etc.

Step (8);

The compound of the formula (g) is reacted in the same manner as in steps (1) and (2) and then in the same manner as in step (4) to be converted into a 11,12-cyclic carbonate, which is reacted in the same manner as in step (3), whereby there can be produced a compound of the present invention of the formula (i):

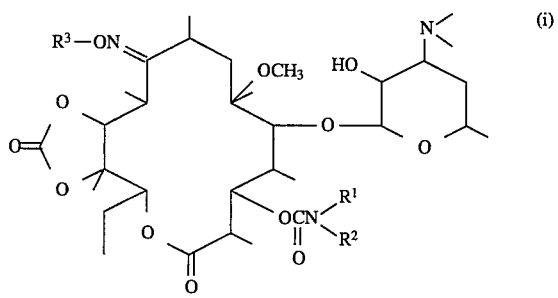

wherein $R^3$ is as defined above.

Step (9);

The compound obtained in step (6) is reacted in the same manner as in step (1) to protect the hydroxyl group at the 2'-position and the hydroxyl group of the oxime at the 9-position, after which the reaction product is reacted in the same manner as in steps (2) and then (3), whereby there can be produced a compound of the present invention of the formula (j):

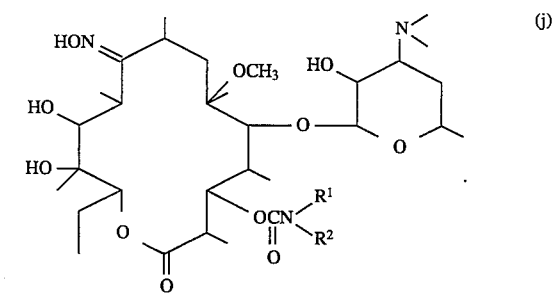

Step (10);

The compound obtained in step (6) is reacted in the same manner as in step (1) to protect the hydroxyl group at the 2'-position and the hydroxyl group of the oxime at the 9-position, after which the reaction product is reacted in the same manner as in steps (2), (4) and then (3), whereby there can be produced a compound of the present invention of the formula (k):

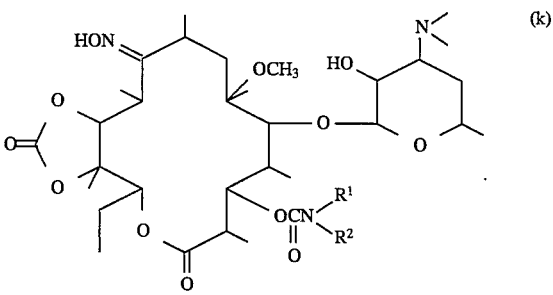

The compounds of the present invention can be administered orally or parenterally. Their pharmaceutical forms for administration are tablets, capsules, powders, troches, ointments, suspensions, suppositories, injections, etc. These can be prepared by conventional preparation techniques.

INDUSTRIAL APPLICABILITY

The compounds of the present invention have a strong antibacterial activity against erythromycin-sensitive bacteria and resistant bacteria. Therefore, the compounds of the present invention are useful as antibacterial agents for curing infectious diseases caused by bacteria in human beings and animals (including farm animals).

BEST MODE FOR CARRYING OUT THE INVENTION

The present invention is illustrated below in further detail with examples.

EXAMPLE 1

Production of
3-O-(2,3,4,5,6-pentafluorophenyl)aminocarbonyl-
5-O-desosaminyl-6-O-methylerythronolide A
11,12-cyclic carbonate (1) 2.27 Milliliters (0.024 mole) of 5-O-desosaminyl-6-O-methylerythronolide A acetic anhydride was added, followed by stirring at room temperature for 6 hours. Acetone was evaporated under reduced pressure and the residue was extracted with dichloromethane. The dichloromethane layer was washed with a saturated sodium hydrogencarbonate solution and then a saturated aqueous sodium chloride solution, and dried over anhydrous magnesium sulfate, after which the solvent was evaporated under reduced pressure. The residue was recrystallized from ether-n-hexane to obtain 12.17 g of 2'-O-acetyl-5-O-desosaminyl-6-O-methylerythronolide as white powder.

mp; 158°–160° C.

Mass (FAB) m/z; 632 [MH]$^+$ $^1$H-NMR (200 MHz, CDCl$_3$) δ (ppm); 2.07 (3H, s), 2.26 (6H, s), 2.95 (3H, s), 3.26 (1H, s), 3.96 (1H, s)

IR (KBr, cm$^{-1}$); 3469, 1750, 1733, 1693

(2) In 25 ml of dichloromethane was dissolved 1.90 g (3.0 mmoles) of the compound obtained in (1) above, and 3.63 ml (45 mmoles) of pyridine and 0.90 ml (7.5 mmoles) of trichloromethyl chloroformate were added under ice-cooling and stirred for 3 hours. After 2.75 g (15 mmoles) of 2,3,4,5,6-pentafluoroaniline was added, the resulting mixture was stirred at room temperature for 15 hours. A piece of ice and 0.5 g of sodium hydrogencarbonate were added, followed by extraction with ethyl acetate. The extract was purified by a silica gel column chromatography (eluent; hexane:acetone:triethylamine= 10:6:0.2) to obtain 1.29 g of 2'-O-acetyl-3-O-(2,3,4,5,6-pentafluorophenyl)aminocarbonyl- 5-O-desosaminyl-6-O-methylerythronolide A 11,12-cyclic carbonate.

(3) In 30 ml of methanol was dissolved 450 mg (0.52 mmole) of the compound obtained in (2) above and the resulting solution was stirred for 24 hours, after which the solvent was evaporated to obtain 375 mg of the title compound.

mp; 227°–229° C. (crystallized from methanol)

Mass (FAB) m/z; 825 [MH]$^+$ $^1$H-NMR (300 MHz, CDCl$_3$) δ (ppm); 2.30 (6H, s), 2.99 (3H, s)

IR (KBr, cm$^{-1}$); 3420, 1813, 1747, 1721

EXAMPLE 2

Production of
3-O-imidazolylcarbonyl-5-O-desosaminyl-
6-O-methylerythronolide A
9-[O-(2,4,6-trimethylbenzyl)oxime]

(1) In 1 liter of 1N hydrochloric acid was dissolved 500 g (0.655 mole) of 6-O-methylerythromycin A 9-oxime, and the solution was allowed to stand at room temperature for 24 hours. Then, the solution was adjusted to pH 10 with an aqueous sodium hydroxide solution, and the crystals precipitated were collected by filtration. The crystals were dissolved in dichloromethane and the resulting solution was washed with a saturated aqueous sodium chloride solution and then dried over anhydrous magnesium sulfate. Subsequently, the dichloromethane was evaporated under reduced pressure and the residue was crystallized from methanol to obtain 259.8 g of 5-O-desosaminyl-6-O-methylerythronolide A 9-oxime as white powder.

mp; 257°–260° C.

Mass (FAB) m/z; 605 [MH]$^+$ $^1$H-NMR (300 MHz, CDCl$_3$) δ (ppm); 1.42 (3H, s), 2.34 (6H, s), 2.99 (3H, s), 3.26 (1H, s), 3.57 (1H, s), 4.37 (1H, s), 4.42 (1H, d, J=7 Hz), 5.23 (1H, dd, J=11 Hz, 2Hz), 7.43 (1H, broad-s)

IR (KBr, cm$^{-1}$); 3523, 3370, 1712, 1188, 1169, 1085

(2) In 20 ml of N,N-dimethylformamide were dissolved 1.73 g (2.87 mmoles) of the compound obtained in (1) above and 7.26 mg (4.30 mmoles) of 2,4,6-trimethylbenzyl chloride, followed by adding thereto 138 mg (344 mmoles) of 60% sodium hydride, and the reaction was carried out at room temperature for 6 hours to obtain 2.34 g of 5-O-desosaminyl-6-O-methylerythronolide A 9-[0-(2,4,6-trimethylbenzyl)oxime] as a white foamy substance.

(3) In 20 ml of acetone, 2.34 g (3.18 mmoles) of the compound obtained in (2) above was reacted with 0.39 ml (4.13 mmoles) of acetic anhydride to obtain 1.74 g of 2'-O-acetyl-5-O-desosaminyl-6-O-methylerythronolide A 9-[O-(2,4,6-trimethylbenzyl)oxime] as a white foamy substance.

(4) In 12 ml of dichloromethane was dissolved 900 mg (1.16 mmoles) of the compound obtained in (3) above, followed by adding thereto 40 mg (5.8 mmoles) of 1,1'-carbonyldiimidazole and 156 mg (1.28 mmoles) of 4-dimethylaminopyridine, and the resulting mixture was heated under reflux for 7.5 hours. Purification by a silica gel column chromatography (eluent; chloroform:methanol:ammonia= 20:1:0.3) gave 117 mg of the title compound and 290 mg of 2'-O-acetyl-3-O-imidazolylcarbonyl- 5-O-desosaminyl-6-O-methylerythronolide A 9-[O-(2,4,6-trimethylbenzyl)oxime] as white foamy substances. The title compound:

$^1$H-NMR (200 MHz, CDCl$_3$) δ (ppm); 2.26 (3H, s), 2.37 (9H, s), 2.41 (3H, s), 2.99 (3H, s), 4.06 (1H, s), 5.70 (2H, s), 6.85 (2H, s), 7.11 (1H) 2'-O-acetyl-3-O-imidazolylcarbonyl-5-O-desosaminyl-6-O-methylerythronolide A 9-[0-(2,4,6-trimethylbenzyl)oxime]:

$^1$H-NMR (200 MHz, CDCl$_3$) δ (ppm); 2.20 (3H, broad-s), 2.26 (3H, s), 2.36 (12H, s), 2.98 (3H, s), 3.29 (1H, s), 4.60 (1H, s), 5.70 (2H, s), 6.84 (2H, s), 7.19 (1H), 7.49 (1H), 8.20 (1H)

EXAMPLE 3

Production of
3-O-(2,4-difluorophenyl)aminocarbonyl-
5-O-desosaminyl-6-O-methylerythronolide A
11,12-cyclic carbonate (1) In 500 ml of dichloromethane was dissolved 50 g (84.8 mmoles) of the compound obtained in Example 1, (1), and 102.6 ml (1.27 moles) of pyridine was added under ice-cooling. At the same temperature, 40 ml of a solution of 25.4 ml (212 mmoles) of trichloromethyl chloroformate in dichloromethane was added dropwise, and the resulting mixture was stirred for 5.5 hours. Small amounts of cold water and a saturated sodium hydrogencarbonate solution were added to the reaction mixture, followed by extraction with dichloromethane. The dichloromethane layer was washed with a saturated sodium hydrogencarbonate solution and then a saturated aqueous sodium chloride solution and dried over anhydrous magnesium sulfate, after which the solvent was evaporated under reduced pressure.

The residue was purified by a silica gel column chromatography (eluent; acetone:n-hexane:triethylamine= 6-10:10:0.2) to obtain 41.93 g of 2'-O-acetyl-5-O-desosaminyl-6-O-methylerythronolide A 11,12-cyclic carbonate as a white foamy substance.

$^1$H-NMR (200 MHz, CDCl$_3$) δ (ppm); 2.05 (3H, s), 2.25 (6H, s), 2.92 (3H, s), 4.57 (1H, d, J=9 Hz), 4.74 (1H, s), 4.75 (1H, dd, J=10 Hz, 9 Hz), 5.13 (1H, dd, J=12 Hz, 2 Hz)

(2) In 10 ml of tetrahydrofuran was dissolved 450 mg (0.685 mmole) of the compound obtained in (1) above, followed by adding thereto 0.41 ml (3.425 mmoles) of 2,4-difluorophenyl isocyanate and 0.08 ml (1.028 mmoles) of pyridine, and the resulting mixture was stirred at room temperature for 18 hours. The reaction mixture was extracted with ethyl acetate, and the extract was washed with a saturated aqueous sodium chloride solution and then purified by a silica gel column chromatography (eluent; chloroform:methanol:25% aqueous ammonia=20:1:0.1).

(3) In methanol, 40 mg of the compound obtained in (2) was heated under reflux for 3 hours to remove the acetyl group, whereby 40 mg of the title compound was obtained as a white foamy substance.

$^1$H-NMR (200 MHz, CDCl$_3$) δ (ppm); 1.30 (3H, s), 2.22 (6H, s), 3.03 (3H, s), 4.03 (1H, d, J=7 Hz), 4.76 (1H, s), 5.02 (1H, d, J=9 Hz), 6.82–6.95 (2H), 7.18 (1H, broad-s), 8.02–8.15 (1H)

EXAMPLE 4

Production of 3-O-(3-nitrophenyl)aminocarbonyl-5-O-desosaminyl-6-O-methylerythronolide A 11,12-cyclic carbonate 1.65 Grams of the title compound was obtained by using a combination of 1.90 g (3.0 mmoles) of the compound obtained in Example 1, (1), 3.63 ml (45 mmoles) of pyridine and 0.90 ml (7.5 mmoles) of trichloromethyl chloroformate, and then 2.07 g (15 mmoles) of 3-nitroaniline, and reacting them in the same manner as in Example 1.

Mass (FAB) m/z; 780 [MH]$^+$ $^1$H-NMR (300 MHz, CDCl$_3$) δ (ppm); 2.18 (6h, s), 3.04 (3H, s), 7.79 (1H, broad-s), 7.51 (1H, m), 7.88 (1H, m), 7.93 (1H, m), 8.38 (1H, m)

IR (KBr, cm$^{-1}$); 3346, 1818, 1742, 1706

EXAMPLE 5

Production of 3-O-[2-(dimethylamino)ethyl]-aminocarbonyl-5-O-desosaminyl-6-O-methylerythronolide A 11,12-cyclic carbonate 0.86 Gram of the title compound was obtained by using a combination of 1.90 g (3.0 mmoles) of the compound obtained in Example 1, (1), 3.63 ml (45 mmoles) of pyridine and 0.90 ml (7.5 mmoles) of trichloromethyl chloroformate, and then 1.63 g (15 mmoles) of N,N-dimethylethylenediamine, and reacting them in the same manner as in Example 1.

Mass (FAB) m/z; 730 [MH]$^+$ $^1$H-NMR (300 MHz, CDCl$_3$) δ (ppm); 2.26 (6H, s), 2.30 (6H, s), 3.02 (3H, s), 5.43 (1H, t)

IR (KBr, cm$^{-1}$); 3387, 1815, 1738, 1713

EXAMPLE 6

Production of 3-O-[2-(dimethylamino)ethyl]aminocarbonyl 5-O-desosaminyl-6-methylerythronolide A In 25 ml of tetrahydrofuran was dissolved 2.95 g (5.0 mmoles) of 5-O-desosaminyl-6-O-methylerythronolide A, followed by adding thereto 2.43 g (15 mmoles) of N,N'-carbonyldiimidazole, and the resulting mixture was refluxed for 5 hours. After extraction with ethyl acetate, the solvent was evaporated and the excess N,N'-carbonyldiimidazole was removed by a silica gel column chromatography (eluent; acetone:chloroform). In 20 ml of ethyl acetate was dissolved 2.96 g of the thus obtained colorless caramel, followed by adding thereto 1.09 g (10.0 mmoles) of N,N-dimethylethyldiamine, and the resulting mixture was stirred at room temperature for 3 days. After extraction with ethyl acetate, the extract was purified by a silica gel column chromatography (eluent; 8–15% methanolchloroform) to obtain 0.53 g of the title compound as colorless crystalline powder.

Mass (FAB) m/z; 704 [MH]$^+$ $^1$H-NMR (300 MHz, CDCl$_3$) δ (ppm); 2.23 (6H, s), 2.28 (6H, s), 3.06 (3H, s)

IR (KBr, cm$^{-1}$); 3455, 3327, 1738, 1723, 1697

EXAMPLE 7

Production of 3-O-(3-aminopropyl)aminocarbonyl-5-O-desosaminyl-6-O-methylerythronolide A (1) In a mixed solution of 15 ml of dichloroethane and 10 ml of tetrahydrofuran was dissolved 1.26 g (2.0 mmoles) of the compound obtained in Example 1, (1), followed by adding thereto 1.30 g (8 mmoles) of N,N'-carbonyldiimidazole, and the resulting mixture was heated under reflux for 8 hours. The solvent was evaporated and the residue was subjected to a silica gel column chromatography (eluent; acetone:hexane:triethylamine= 5:10:0.1) to obtain 1.14 g of 2'-O-acetyl- 3-O-imidazolylcarbonyl-5-O-desosaminyl-6-O-methylerythronolide A.

(2) In 10 ml of tetrahydrofuran was dissolved 1 g of the compound obtained in (1) above, followed by adding thereto 0.22 ml (2.5 mmoles) of 1,3-diaminopropane, and the resulting mixture was stirred at room temperature for 16 hours. The solvent was evaporated under reduced pressure, and the residue was extracted with methylene chloride. Then, the extract was purified by a silica gel column chromatography (eluent; chloroform:methanol:aqueous ammonia= 100:20:0.5) to obtain 0.74 g of the title compound which was colorless and foamy.

Mass (FAB) m/z; 690 [MH]$^+$ $^1$H-NMR (300 MHz, CDCl$_3$) δ (ppm); 2.28 (6H, s), 3.05 (3H, s)

IR (KBr, cm$^{-1}$); 3414, 1724

EXAMPLE 8

Production of
3-O-(2,3-dihydroxypropyl)aminocarbonyl-
5-O-desosaminyl-6-O-methylerythronolide A In a mixed solution of 15 ml of tetrahydrofuran and 10 ml of N,N-dimethylformamide was dissolved 1.81 g (2.5 mmoles) of a compound obtained in the same manner as in Example 7, (1), followed by adding thereto 683 mg (7.5 mmoles) of 3-amino-1,2-propanediol, and the resulting mixture was stirred at room temperature for 20 hours. The solvent was evaporated under reduced pressure, and the residue was extracted with ethyl acetate. The solvent was evaporated and 1.72 g of the colorless and foamy compound thus obtained was dissolved in 10 ml of methanol, after which the resulting solution was stirred for 15 hours. The solvent was evaporated and the residue was purified by a silica gel column chromatography (eluent; chloroform:methanol:aqueous ammonia=100:10:0.1) to obtain 1.17 g of the title compound which was colorless and foamy.

Mass (FAB) m/z; 707 [MH]$^+$ $^1$H-NMR (300 MHz, CDCl$_3$) δ (ppm); 2.48 (6H, s), 3.04 (3H, s)

IR (KBr, cm$^{-1}$); 3436, 1735

EXAMPLE 9

Production of
3-O-[(3-amino-2-hydroxy)propyl]-aminocarbonyl-
5-O-desosaminyl-6-O-methylerythronolide A 0.82 Gram of the title compound which was colorless and foamy was obtained by using 1.5 g (2.07 mmoles) of a compound obtained in the same manner as in Example 7, (1) and 372 mg (4.13 mmoles) of 1,3-diamino-2-propanol, and reacting them in the same manner as in Example 8.

Mass (FAB) m/z; 706 [MH]$^+$ $^1$H-NMR (300 MHz, CDCl$_3$) δ (ppm); 2.30 (6H, s), 3.04 (3H, s), 5.71 (1H, broad-s)

IR (KBr, cm$^{-1}$); 3437, 1808, 1736

EXAMPLE 10

Production of
3-O-(1-methylpiperazin-4-yl)carbonyl-
5-O-desosaminyl-6-O-methylerythronolide A 1.43 Grams of the title compound was obtained by using 3.2 g (4.41 mmoles) of a compound obtained in the same manner as in Example 7, (1) and 1.94 ml (17.6 mmoles) of 1-methylpiperazine, and reacting them in the same manner as in Example 8.

Mass (FAB) m/z; 716 [MH]$^+$ $^1$H-NMR (300 MHz, CDCl$_3$) δ (ppm); 2.33 (9H, s), 3.06 (3H, s)

IR (KBr, cm$^{-1}$); 3459, 1814, 1737, 1703

EXAMPLE 11

Production of
3-O-(1-methylpiperazin-4-yl)carbonyl-
5-O-desosaminyl-6-O-methylerythronolide A
11,12-cyclic carbonate (1) In 15 ml of acetone was dissolved 1.26 g of the compound obtained in Example 10, followed by adding thereto 0.25 ml (2.64 mmoles) of acetic anhydride, and the resulting mixture was stirred at room temperature for 20 hours. Extraction with ethyl acetate gave 1.31 g of anhydrous and foamy 2'-O-acetyl-3-O-(1-methylpiperazin-4-yl)carbonyl-5-O-desosaminyl-6-O-methylerythronolide A.

(2) In 20 ml of dichloromethane was dissolved 1.31 g of the compound obtained in (1) above, and 2.13 ml (26.4 mmoles) of pyridine and 0.53 ml (4.4 mmoles) of trichloromethyl chloroformate were added under ice-cooling and stirred for 3 hours. A piece of ice and sodium hydrogencarbonate powder were added and the pH of the aqueous layer was adjusted to 7, after which the solvent was evaporated under reduced pressure. After extraction with ethyl acetate, the solvent was again evaporated under reduced pressure. The residue was purified by a silica gel column chromatography (eluent; 5–10% methanol-chloroform) to obtain 0.81 g of 2'-O-acetyl- 3-O-(1-methylpiperazin-4-yl)carbonyl-5-O-desosaminyl- 6-O-methylerythronolide A 11,12-cyclic carbonate.

(3) 0.54 Gram of the title compound was obtained by dissolving 0.81 g of the compound obtained in (2) above, in 20 ml of methanol, and stirring the resulting solution for one day.

Mass (FAB) m/z; 742 [MH]$^+$ $^1$H-NMR (300 MHz, CDCl$_3$) δ (ppm); 2.30 (6H, s), 2.32 (3H, s), 3.02 (3H, s)

IR (KBr, cm$^{-1}$); 3459, 1814, 1742, 1704

EXAMPLE 12

Production of 3-O-(2-cyanoimino-1,3-oxazolidin-
4-yl)methylaminocarbonyl-5-O-desosaminyl-6-O-
methylerythronolide A In 10 ml of ethanol was dissolved 353 mg (0.5 mmole) of the compound obtained in Example 9, and 146 mg (1.0 mmole) of S,S'-dimethyl-N-cyanodithioiminocarbonate was added and then stirred for 7 hours. The solvent was evaporated under reduced pressure, and the residue was extracted with ethyl acetate. By a silica gel column chromatography (eluent; chloroform:methanol:aqueous ammonia=) 20:1:0.1), 318 mg of the title compound was obtained.

Mass (FAB) m/z; 757 [MH]$^+$ $^1$H-NMR (300 MHz, CDCl$_3$) δ (ppm); 2.30 (6H, s), 3.05 (3H, s), 5.55 (1H, broad-s)

IR (KBr, cm$^{-1}$); 3424, 2195, 1738, 1656

Test Example (in vitro antibacterial activity)

The in vitro antibacterial activity of the compound of the present invention against various test bacteria was measured according to the MIC measuring method of Japanese Chemotherapeutic Association by using sensitive disc media (available from Eiken Chemical, Co.). 6-O-methylerythromycin A was used as a reference agent. The results are expressed in MIC values (minimum inhibitory concentration; mcg/ml).

TABLE 1

| | in vitro Antibacterial activity MIC value (mcg/ml) | |
|---|---|---|
| | Compound | |
| Microorganism | Example 1 | Reference agent |
| S. aureus 209P-JC | 0.05 | 0.10 |
| S. aureus Smith 4 | 0.10 | 0.10 |
| S. epidermides IID 866 | 0.10 | 0.10 |
| E. faecalis CSJ 1212 | 0.39 | 0.78 |

TABLE 1-continued

| in vitro Antibacterial activity MIC value (mcg/ml) | | |
|---|---|---|
| | Compound | |
| Microorganism | Example 1 | Reference agent |
| S. aureus J-109 | 100 | >100 |
| S. aureus B1 | 0.78 | >100 |
| S. aureus C1 | 0.78 | >100 |

We claim:

1. A 5-O-desosaminylerythronolide derivative represented by the formula:

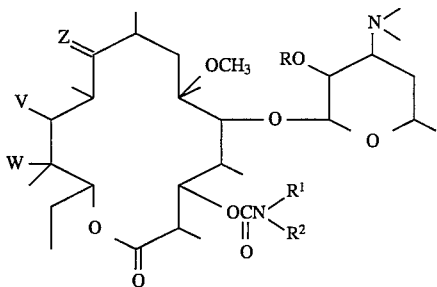

wherein:
each of $R^1$ and $R^2$ is a hydrogen atom; a phenyl group; a substituted phenyl group having 1 to 5 substituents selected from the group consisting of halogen atoms, nitro groups and amino groups; a $C_1$–$C_{15}$ alkyl group; a $C_2$–$C_{15}$ alkyl group substituted by one member selected from the group consisting of amino, dimethylamino, benzylamino, N-benzyl-N-methylamino, dibenzylamino and hydroxy; a $C_7$–$C_{15}$ aralkyl group; or a $C_7$–$C_{15}$ aralkyl group substituted by one member selected from the group consisting of nitro, methoxy, methylthio, amino and dimethylamino or $R^2$ and $R^2$ together form a 5 or 6 membered ring together with the adjacent nitrogen atom, Z is an oxygen atom or a group represented by the formula =N—O—$R^3$, wherein $R^3$ is a hydrogen atom; a $C_1$–$C_8$ alkyl group; a benzyl group; or a substituted benzyl group having 1 to 5 substituents selected from the group consisting of halogen atoms and $C_1$–$C_4$ alkyl groups, V is a hydroxyl group; and W is a hydrogen atom or a hydroxyl group, or V and W represent, together with the carbon atoms at the 11- and 12-positions, a group represented by the formula:

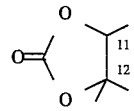

or a group represented by the formula:

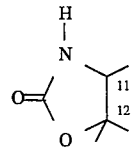

R is a hydrogen atom, a $C_2$–$C_{15}$ alkoxycarbonyl group, a 2-methoxyethoxycarbonyl group a 2-[2-(2-methoxyethoxy)ethoxy] ethoxycarbonyl group, a 2-[2-(2-ethoxyethoxy)ethoxy]ethoxycarbonyl group, an acetyl group, a propionyl group, benzoyl group, an ethylsuccinyl group, or a pyridylcarbonyl group or a pharmaceutically acceptable acid addition salt thereof.

2. A 5-O-desosaminylerythronolide derivative according to claim 1 wherein the substituted $C_2$–$C_{15}$ alkyl group is an aminoethyl group, a dimethylaminoethyl group, a benzylaminoethyl group, an N-benzyl -N-methylaminoethyl group, a dibenzylaminoethyl group, a 2,3-dihydroxypropyl group, a 3-aminopropyl group or a 2-hydroxy-3-aminopropyl group; and the $C_7$–$C_{15}$ substituted aralkyl group is a nitrobenzyl group, a methoxybenzyl group, an aminobenzyl group or a dimethylaminobenzyl group.

* * * * *

UNITED STATES PATENT AND TRADEMARK OFFICE
CERTIFICATE OF CORRECTION

PATENT NO. : 5,523,399
DATED : June 4, 1996
INVENTOR(S) : ASAKA et al

It is certified that error appears in the above-indentified patent and that said Letters Patent is hereby corrected as shown below:

On the title page, item

"[22] PCT Filed: December 15, 1992" should read
--[22] PCT Filed: December 25, 1992--.

Col. 13, line 40, "$R^2$", first instance, should read --$R^1$--.

Signed and Sealed this

Fifteenth Day of July, 1997

Attest:

BRUCE LEHMAN

Attesting Officer

Commissioner of Patents and Trademarks